United States Patent
Jiang

(10) Patent No.: US 6,330,301 B1
(45) Date of Patent: Dec. 11, 2001

(54) OPTICAL SCHEME FOR HIGH FLUX LOW-BACKGROUND TWO-DIMENSIONAL SMALL ANGLE X-RAY SCATTERING

(75) Inventor: Licai Jiang, Rochester Hills, MI (US)

(73) Assignee: Osmic, Inc., Troy, MI (US)

( * ) Notice: Subject to any disclaimer, the term of this patent is extended or adjusted under 35 U.S.C. 154(b) by 0 days.

(21) Appl. No.: 09/466,261

(22) Filed: Dec. 17, 1999

(51) Int. Cl.[7] .................................................. G21K 1/06
(52) U.S. Cl. ............................ 378/85; 378/84; 378/145
(58) Field of Search .................................. 378/34, 84, 85, 378/145, 147, 148, 150, 154, 157, 160

Primary Examiner—Robert H. Kim
Assistant Examiner—Coutney Thomas
(74) Attorney, Agent, or Firm—Brinks Hofer Gilson & Lione

(57) ABSTRACT

An x-ray analysis system including a focusing optic for focusing an x-ray beam to a focal point, a first slit optically coupled to the focusing optic, a second slit optically coupled to the first slit, and an x-ray detector, where the focal point is located in front of the detector.

20 Claims, 2 Drawing Sheets

US 6,330,301 B1

OPTICAL SCHEME FOR HIGH FLUX LOW-BACKGROUND TWO-DIMENSIONAL SMALL ANGLE X-RAY SCATTERING

BACKGROUND OF THE INVENTION

The present invention relates to an x-ray analysis application. More specifically, the present invention relates to an apparatus and method for generating, forming, and directing an x-ray beam used in x-ray analysis.

A common method used to study moderately ordered structures, i.e. those structures which have short range ordering but lack long range ordering, is small angle x-ray scattering. The method is based on illuminating a sample structure with a beam of x-rays. A portion of the x-ray beam is not able to travel directly through the sample structure, rather some rays are deflected or scattered and emerge from the sample at varying angles. The incident x-rays make their way along the spaces between the atoms of the structure or are deflected by the atoms. Since the structure is ordered throughout with short range ordering, the scattering from the structure will create a diffused x-ray pattern at a very close range to the x-rays traveling directly through the structure. This diffused pattern corresponds to the atomic structural arrangement of the sample.

Small angle x-ray scattering can be done in one or two dimensions. One dimensional small angle x-ray scattering utilizes a line source to maximize x-ray flux. The resultant diffusion pattern formed by the line source reveals information in only one dimension. Two dimensional x-ray scattering utilizes an x-ray point source which makes it possible to reveal two dimensional information. Although a rotating anode is preferred as a laboratory x-ray point source, other x-ray generators, including sealed tubes, may be used. A synchrotron has also been used in two-dimensional applications due to its well-collimated and high intensity beam.

Traditionally, an x-ray beam used in two dimensional small angle scattering is formed by a series of slits or pinholes to collimate the divergent beam and limit scattering effects from the slits. For samples with strong scattering power or a large scattering angle, such as crystals, parasitic scattering from pinholes and mirrors can be ignored. A two pinhole system may be used in such an application. For samples with weak scattering power or a small scattering angle, such as those contemplated by the present invention, a three pinhole system is preferably used. The current techniques for small angle scattering involve the use of pinhole systems, filters, and total reflection mirrors. A Ni filter, graphite or other crystals are used in a pinhole system or a pinhole+total reflection mirror system to reduce the K$\beta$ radiation or other continuous spectrum radiation. Total reflection mirrors such as Kirkpatrick-Baez or cross-coupled mirrors are frequently used with the pinhole systems (both with two-pinhole systems and three pinhole systems). Presently, the focal point of a total reflection mirror used with a pinhole system is always set at the detector position, creating a loss of flux. Parabolic multilayer optics (Kirkpatrick-Baez, or cross-coupled) are also used in small angle scattering systems but fail to enhance the beam at the sample position effectively.

Small angle x-ray scattering systems presently used in the art suffer from noise problems caused by pinhole scattering and limited x-ray flux used for generating x-ray scattering patterns. Thus, there is a need in the art for a small angle x-ray scattering system which eliminates diffraction noise and increases the flux on a sample.

SUMMARY OF THE INVENTION

The present invention is a method and apparatus for generating an x-ray beam used in small angle x-ray scattering applications. The present invention uses optics to focus and increase the flux of an x-ray beam generated by an x-ray point source and a system of slits or pinholes to shape the x-ray beam. The optical system can be configured in either a two pinhole system for maximum flux or a three pinhole system for low background noise and a small minimum accessible angle.

An object of the present invention is to reduce the beam divergence of an x-ray beam used in small angle x-ray scattering applications.

A further object of the present invention is to increase the flux of an x-ray beam on a sample in small angle x-ray scattering applications.

A still further object of the present invention is to have a small "minimum accessible angle."

BRIEF DESCRIPTION OF THE DRAWINGS

The various advantages of the present invention will become apparent to those skilled in the art after reading the following specification and by reference to the drawings, in which.

DETAILED DESCRIPTION OF THE PREFERRED EMBODIMENT

Figure 1:
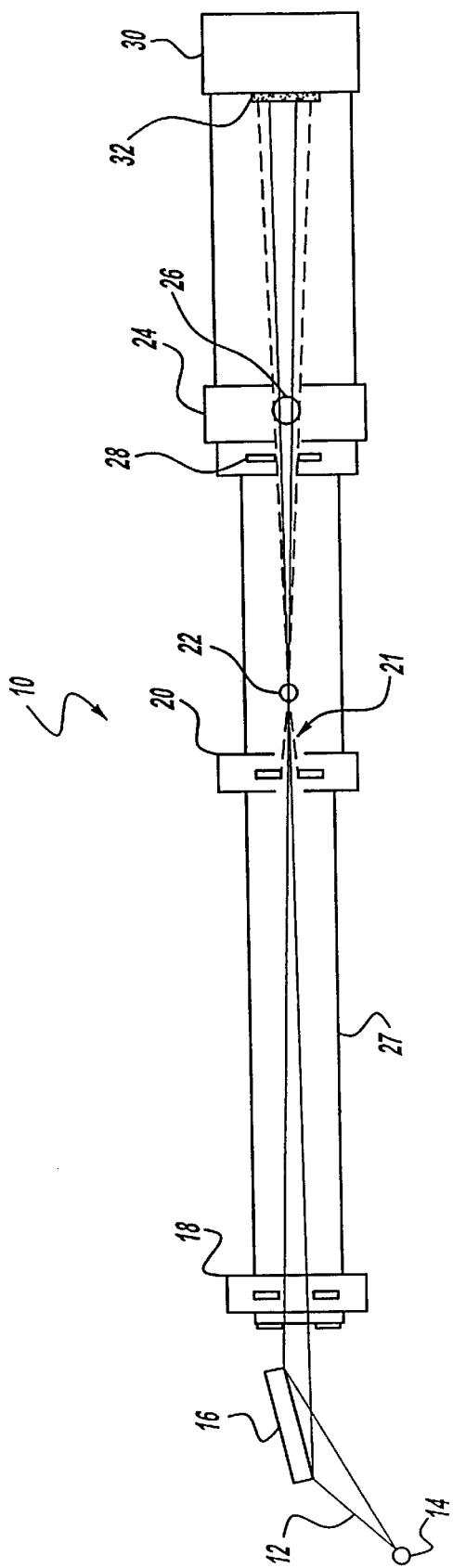
FIG. 1 is a diagrammatic view of the optical scheme of the present invention according to the preferred embodiment.
Figure 2:
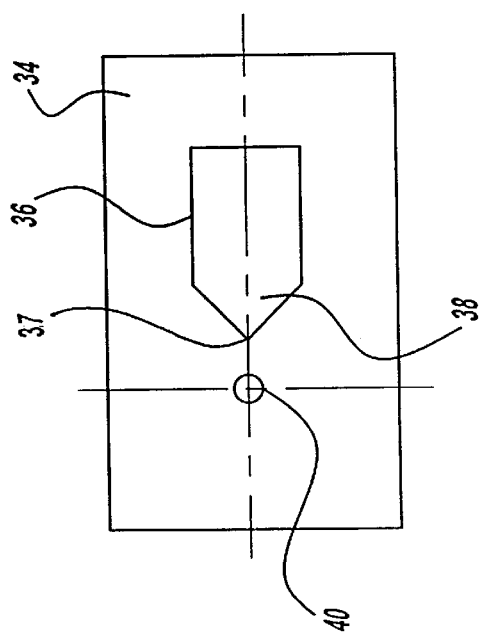
FIG. 2 is a diagrammatic view of the alignment mechanism of the present invention according to the preferred embodiment.

FIG. 1 is a diagrammatic view of the optical system 10 of the present invention. An x-ray beam 12 is generated by an x-ray source 14 that is directed towards an optic 16, such as an elliptical mirror, that focuses the x-ray beam 12. The optic 16 has a reflective surface which may be comprised of bent graphite, bent perfect crystal, a total reflection mirror, a mulitlayer Bragg reflector which may be depth or laterally graded, or any other x-ray reflective surface known in the art. The optic 16 directs the x-ray beam through a first slit (or pinhole) 18 and a second slit (or pinhole) 20 to form and define a coherent x-ray beam 21. Scattering and interference patterns or noise created by the first slit 18 are blocked by the second slit 20. The focal point 22 of the x-ray beam 21 is located between the second slit 20 and an x-ray detector 30. A sample chamber 24, containing a sample structure 26 to be analyzed, includes a third slit 28 to eliminate scattering and interference patterns created by the second slit 20.

The x-ray beam 21 flux at the sample chamber 24 and the x-ray beam 21 size or incident area on the x-ray detector 30 depend on where the focal point 22 of the optic 16 is located. Flux passing through the second slit 20 and reaching the sample chamber 24 is the greatest when the focal point 22 of the optic 16 is positioned on the second slit 20, and the x-ray beam 21 size on the x-ray detector 30 is also the greatest in this situation. The x-ray beam 21 size on the x-ray detector 30 is the smallest if the focal point 22 of the optic 16 is positioned on or at the x-ray detector 30, therefore the resolution of a system using this focal point 22 position would be the greatest. However, the flux in this case would also be the smallest. Therefore, the position of the focal point 22 in the system is determined by the trade-off between intensity and resolution of x-rays incident on the x-ray detector 30.

In certain cases, due to the intrinsic divergence of the x-ray beam 21, the resolution would reach its limit at certain positions of the focal point 22. Accordingly, moving the focal point 22 closer to x-ray detector 30 would not improve the resolution and would only reduce the flux. Thus, in this case, there would be no benefit to focus the x-ray beam 21 on the x-ray detector 30. Since the minimum accessible angle of the system is determined by the slit (pinhole) configuration, it is independent of the position of the focus.

The first and second slits 18 and 20 of the optical system 10 determine the size and shape of the x-ray beam 21 and the third slit 28 blocks parasitic scattering. The x-ray beam 21, because of its focused nature, enables maximum flux to be concentrated on the sample structure 26. The x-ray detector 30 is able to detect the diffusion pattern created by the small angle scattering from the sample structure 26 because of the increased flux on the sample structure 26 and the elimination of divergence and scattering. The x-ray detector 30 is further equipped with a beam stopper 32 to prevent direct x-ray beam damage to the x-ray detector 30 and noise. The exact location of the focal point 22 between the second slit 20 and the x-ray detector 30 depends on the desired flux and resolution characteristics of the optical system 10.

The optical system 10 of the present invention is preferably enclosed in a vacuum path or pre-flight beam pipe 27 to eliminate scattering and absorption caused by atmospheric gases and particles. The pre-flight beam pipe 27 is comprised of a number of individual pipes which may be mixed and matched to optimize and change the length of the system.

The slits 18, 20, and 28 in the preferred embodiment, are formed as pinholes that are precision machined as round holes. Rounded pinholes create significant difficulty in alignment, especially when the sizes of the pinholes are small and multiple pinholes are used. The present invention includes a pinhole plate 34 having an alignment window 36 equipped with a triangle shaped nose 38 offset and aligned with a pinhole 40. During alignment of an x-ray beam, the x-ray beam is adjusted to enter and exit the alignment window 36. An x-ray detector is used as feedback to ensure that the x-ray beam is passing through the alignment window 36. The pinhole plate 34 is then moved manually or automatically in a vertical and horizontal fashion in the direction of the pinhole 40. If the x-ray detector does not detect the x-ray beam during an indexing of the alignment window 36 relative to the x-ray beam, the pinhole plate 34 will be moved to its last position and indexed in the opposite vertical or possibly horizontal direction. In this manner, the x-ray beam position is always known and the x-ray beam may be traversed to the vertex 37 of the triangle 38. The x-ray beam follows, in relative fashion, the cutout of the alignment window 36 until it reaches the vertex 37 of the triangle 38. At the vertex 37 of the triangle 38, movement will block or reduce the flux of the beam in both vertical directions and horizontal movement in the direction of the pinhole 40 will also block or reduce the beam. Accordingly, when such a condition is reached it is known that the beam is at the vertex 37 of the triangle 38.

The pinhole 40 is a known fixed distance from the vertex 37 of the triangle 38. Thus, when the x-ray beam is found to be at the vertex 37 of the triangle 38, the pinhole plate 34 or x-ray beam may be precisely indexed this known distance to the pinhole 40, ensuring precise alignment of the pinhole 40 and the x-ray beam. Accordingly, the position of the x-ray beam will be known.

In a first embodiment, the pinhole plate 34 is manually moved relative to the x-ray beam 21 using a precision x-ray table. The operator will read the x-ray detector 30 output and move the pinhole plate 34 accordingly. In alternate embodiments the operator will move the x-ray beam relative to the pinhole plate 34.

In a second embodiment of the present invention, the pinhole plate 34 is moved using an automated servomotor or linear actuator system. The detector 30 feedback is transmitted to a computer which controls the x-y indexing of the x-ray beam or pinhole plate 34. In response to feedback from the detector 30, the computer will give the actuator system position commands to properly align the x-ray beam 21 and the pinhole plate 34.

Figure 3:
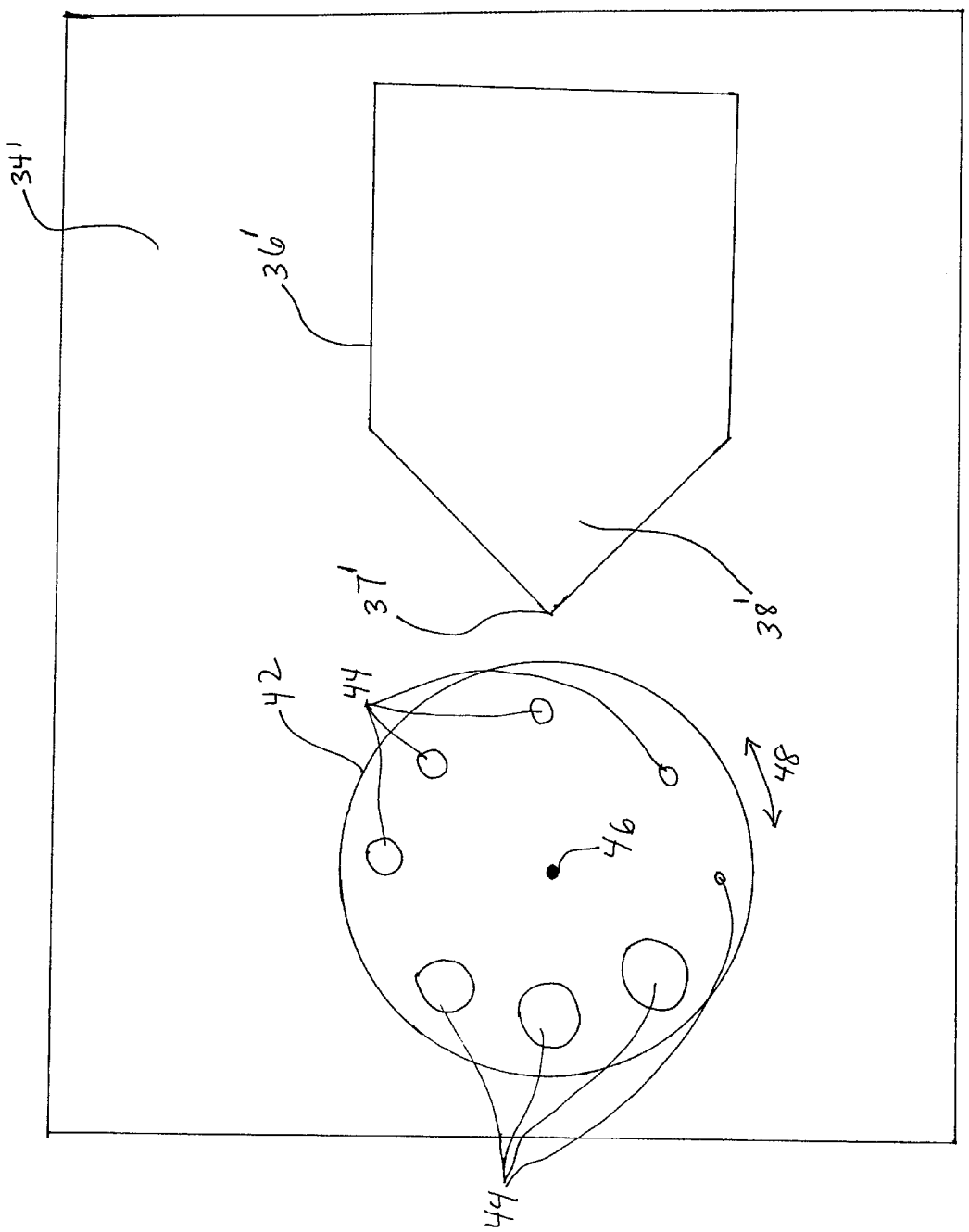
FIG. 3 is a diagrammatic view of an alternate embodiment of the alignment mechanism of the present invention.

Referring to FIG. 3, an alternate embodiment of the pinhole plate 34' of the present invention is shown. The pinhole plate 34', as in the first embodiment 34, includes an alignment window 36' equipped with a triangle shaped nose 38' having a vertex 37'. A rotating aperture plate 42, having multiple apertures 44, rotates about a point 46 in the directions of arrow 48. The rotating aperture plate 42 allows multiple apertures 44 having various aperture diameters to be used in the present invention. Each aperture 44 may be indexed or rotated about point 46 to a position with a known offset from the vertex 37' of the triangle shaped nose 38'. The center of each aperture 44 in the rotating aperture plate 42 is the same radial distance from the point 46, allowing each aperture 44 to be correctly offset from the vertex 37' of the triangle shaped nose 38'. A rotary position feedback device such as an encoder or a manual latch may be used to precisely position the apertures 44 with respect to the vertex 37' of the triangle shaped nose 38'.

It is to be understood that the invention is not limited to the exact construction illustrated and described above, but that various changes and modifications may be made without departing from the spirit and scope of the invention as defined in the following claims.

What is claimed is:

1. An x-ray analysis system comprising:
   a focusing optic for focusing an x-ray beam to a focal point;
   a first slit optically coupled to said focusing optic;
   a second slit optically coupled to said first slit; and
   an x-ray detector, wherein said focal point is located between said second slit and said x-ray detector.

2. The x-ray analysis system of claim 1 further comprising a third guard slit optically coupled to said second slit to block parasitic scattering from said second slit.

3. The x-ray analysis system of claim 1, wherein said focusing optic is a Bragg reflector.

4. The x-ray analysis system of claim 3, wherein said Bragg reflector is a multilayer.

5. The x-ray analysis system of claim 4, wherein said Bragg reflector is depth graded.

6. The x-ray analysis system of claim 4, wherein said Bragg reflector is laterally graded.

7. The x-ray analysis system of claim 1, wherein said focusing optic is a total reflection mirror.

8. The x-ray analysis system of claim 1, wherein said focusing optic has an elliptical surface.

9. The x-ray analysis system of claim 1, wherein said focusing optic is a Kirkpatrick-Baez side-by-side optic.

10. The x-ray analysis system of claim 2, wherein said first, second and third slits are pinholes.

11. A method for reducing diffraction noise in an x-ray analysis system comprising:
    conditioning an x-ray beam with a lens
    directing said x-ray beam through a first aperture;
    directing said x-ray beam through a second aperture; and focusing said x-ray beam with said lens at a point after it exits said second aperture.

12. The method of claim 11 further comprising the step of directing said x-ray beam through a sample structure.

13. The method of claim 12 further comprising the step of detecting said x-ray beam after it exits said sample structure.

14. An apparatus for shaping an x-ray beam comprising:
a plate;
an opening formed in said plate, said opening having an outline which converges to a vertex;
an aperture formed in said plate a known distance from said vertex;
an x-ray detector used as feedback in orienting the x-ray beam,
wherein the x-ray beam is positioned to pass through said opening to said x-ray detector, wherein the x-ray beam and said opening are moved relative to each other, the x-ray beam moved to said vertex using said x-ray detector feedback, and wherein the x-ray beam is moved said known distance to said aperture.

15. The apparatus of claim 14, wherein said opening has a triangular shaped end portion which converges to said vertex.

16. The apparatus of claim 14 further comprising a rotating aperture plate having a plurality of apertures.

17. The apparatus of claim 16, wherein each of said apertures is a different size.

18. A method of directing an x-ray beam through an aperture comprising:

positioning an x-ray beam to travel through an opening formed in a plate, said opening having an outline which converges to a vertex;
observing said x-ray beam with an x-ray detector providing feedback to determine if said x-ray beam is traveling through said opening;
indexing said x-ray beam in relative fashion with respect to said opening until said x-ray beam reaches said vertex of said opening; and
displacing said x-ray beam a known distance to the aperture.

19. An x-ray analysis system comprising:
a focusing optic for focusing an x-ray beam to a focal point;
a first slit optically coupled to said focusing optic;
a second slit optically coupled to said first slit to form and define said x-ray beam in conjunction with said first slit;
a third slit optically coupled to said second slit to block scattering from said second slit;
a sample housing for holding a sample to be illuminated by said x-ray beam; and
an x-ray detector for detecting a scattering pattern created by illuminating said sample, wherein said focal point is located between said second slit and said x-ray detector.

20. The x-ray analysis system of claim 18, wherein said focusing optic is a Bragg reflector.

* * * * *